United States Patent [19]
Francotte

[11] Patent Number: 5,948,904
[45] Date of Patent: Sep. 7, 1999

[54] PROCESS FOR THE PREPARATION OF AROMATIC CARBAMOYL-SUBSTITUTED POLYSACCHARIDE DERIVATIVES

[75] Inventor: Eric Francotte, Nuglar, Switzerland

[73] Assignee: Novartis AG, Basel, Switzerland

[21] Appl. No.: 08/894,971

[22] PCT Filed: Feb. 22, 1996

[86] PCT No.: PCT/EP96/00732

§ 371 Date: Sep. 2, 1997

§ 102(e) Date: Sep. 2, 1997

[87] PCT Pub. No.: WO96/27639

PCT Pub. Date: Sep. 12, 1996

[30] Foreign Application Priority Data

Mar. 7, 1995 [CH] Switzerland ............... 639/95

[51] Int. Cl.$^6$ ................................. C07H 1/00
[52] U.S. Cl. ............ 536/123.1; 536/17.9; 536/18.7; 536/20; 536/30; 536/45; 536/51; 536/53; 536/55.3; 536/56; 536/112; 536/124; 536/126; 536/127
[58] Field of Search .................. 536/17.9, 18.7, 536/20, 30, 45, 51, 53, 55.3, 56, 112, 124, 126, 127, 123.1

[56] References Cited

U.S. PATENT DOCUMENTS

| 4,861,872 | 8/1989 | Okamoto et al. | 536/18.7 |
| 5,354,852 | 10/1994 | Ikeda | 536/17.9 |

FOREIGN PATENT DOCUMENTS

| 0157365 | 10/1985 | European Pat. Off. . |
| 0527236 | 2/1993 | European Pat. Off. . |
| 0552824 | 7/1993 | European Pat. Off. . |

*Primary Examiner*—James O. Wilson
*Attorney, Agent, or Firm*—Stephen G. Kalinchak; William K. Wissing

[57] ABSTRACT

The invention relates to a process for the preparation of polysaccharide-N-arylcarbamates in suitable form as supports for chromatography, which process comprises adding to polysaccharide carbamates, which may be substituted in the aryl moiety, an N-aryl-1-lower-alkylcarbamate-containing solution of an organic solvent, with vigorous stirring, until the polysaccharide derivative is completely dissolved and then adding thereto an aqueous solution containing a high molecular weight surfactant and, with continued stirring, removing the organic solvent from the emulsion so obtained and isolating the solid particles and washing and drying them. The polysaccharide derivatives so obtained can be used as support materials for the chromatographic separation of enantiomers.

22 Claims, No Drawings

PROCESS FOR THE PREPARATION OF AROMATIC CARBAMOYL-SUBSTITUTED POLYSACCHARIDE DERIVATIVES

This is a 371 of international application PCT/EP 96/00732, filed Feb. 22, 1996.

The invention relates to a process for the preparation of aromatic carbamoyl-substituted polysaccharide derivatives which find utility as support materials for the chromatographic separation of enantiomers.

In Chemistry Letters, pp. 739–742 (1984), Y.Okamoto et al describe a separation material suitable for chromatography, which material consists of a macroporous silica gel coated with cellulose triacetate or cellulose tribenzoate. This support material is expensive. In addition, only the cellulose derivative layer is available for the separation of the enantiomers so that the separation capacity is not entirely satisfactory.

In J. of Chromatography, 351, pp. 346–350 (1986), K.-H. Rimböck propose using as stationary phase powdered microcrystalline tribenzoyl cellulose obtained by simple precipitation from a solution. The separation capacity of the powdered material is insufficient. Furthermore, the particle size and the outer particle shape cannot be controlled when this process is used.

EP-A-0 025 639 discloses a process for the preparation of spherical porous cellulose particles. In this process, an organic solution of cellulose triacetate containing a long-chain alcohol is suspended, with stirring, in an aqueous phase containing a high molecular weight surfactant, typically polyvinyl alcohol or gelatin. After removal of the organic solvent, the cellulose triacetate particles so obtained are isolated and purified and then saponified. Our own tests showed that the cellulose triacetate particles obtained according to this process have only a small specific surface area and only low separating power for enantiomers when used as stationary phase in liquid chromatographic processes.

EP-A-0 316 270 discloses finely particulate cellulose esters of aromatic or aromatic-aliphatic carboxylic acids in the form of essentially round partially crystalline particles, which may indeed be used as stationary phase in chromatographic processes, in particular for the separation of enantiomers, but which are not suitable for all compound classes.

EP-A-0 157 364, EP-A-0 147 801 and EP-A-0 157 356 disclose polysaccharide carbamates which are suitable for separating enantiomers, but in the case of said polymers it has to be taken into consideration that they can be used only after being applied to a support, typically silica gel.

EP-A-0 527 236 discloses aromatic and araliphatic polysaccharide carbamates which are used as stationary phase for the chromatographic separation of enantiomers. It is emphasized that the materials so obtained can be used as such without being applied to a support. However, extensive experiments on our part showed that the materials so obtained cannot be used according to the indicated conditions for the chromatographic separation of enantiomers.

The invention relates to a process for the preparation of polysaccharide-N-arylcarbamates in suitable form as supports for chromatography, which process comprises adding to polysaccharide carbamates, which may be substituted in the aryl moiety, a N-aryl-1-lower-alkylcarbamate-containing solution of an organic solvent, with vigorous stirring, until the polysaccharide derivative is completely dissolved and then adding thereto an aqueous solution containing a high molecular weight surfactant and, with continued stirring, removing the organic solvent from the emulsion so obtained and isolating the solid particles and washing and drying them.

The polysaccharide particles are obtained in a particle size of 5–150 $\mu$m and, in particular, of 10–30 $\mu$m in rounded or also in irregular shape.

The specific surface area is preferably 1–100 m$^2$/g, but particularly preferably 3–35 m$^2$/g.

The specific surface area can be influenced by the reaction conditions, typically by the choice of solvent and by the way in which the reaction is carried out, e.g. by the rate of addition, stirring and evaporation, as well as by the ratios of solvent, water and high molecular weight surfactant.

High molecular weight surfactants are preferably polyvinyl alcohol or carboxymethylcellulose. It is also possible to use other surfactants such as those described in National Standard Reference Data System (NSRDS), Nat. Bur. Stand. (U.S.) 36, pages 24–32, U.S. Government Printing Office (1971), typically $C_8$–$C_{16}$ sulfuric acid semiester, e.g. lauryl sulfate.

Surprisingly, the polysaccharide-N-arylcarbamates so obtained can be used in excellent manner as supports for the chromatographic separation of enantiomers without prior application to a support, e.g. silica gel.

The invention relates in particular to a process for the preparation of polysaccharide-N-phenylcarbamates in suitable form as supports for chromatography, which process comprises adding to polysaccharide carbamates, which may be substituted in the phenyl moiety, a N-phenyl-1-heptylcarbamate-containing solution of an organic solvent, preferably methylene chloride, with vigorous stirring, until the polysaccharide derivative is completely dissolved and then adding thereto an aqueous solution containing a high molecular weight surfactant and, with continued stirring, removing the organic solvent from the emulsion so obtained and isolating the solid particles and washing and drying them.

The invention relates in particular to the compounds obtained in the Examples.

In the above as well as hereinafter, lower radicals and compounds will be understood as meaning typically those containing up to and including 7 carbon atoms.

Polysaccharides are typically cellulose, amylose, chitosan, dextran, xylan and inulin, which are available as polysaccharides in a high degree of purity.

It is preferred to use polysaccharides having a degree of polymerisation (number of the pyranose and furanose rings) of at least 5 and, particularly preferably, of at least 10 but, to ensure simple handling, 1000 should not be exceeded.

Lower alkyl is typically $C_1$–$C_4$alkyl, e.g. methyl, ethyl, propyl or butyl, each of which can also be substituted by halogen, typically fluoro or chloro, for example trifluoromethyl and trichloromethyl.

Aryl as such is typically phenyl or naphthyl, e.g. 1- or 2-naphthyl, or substituted phenyl or naphthyl, typically phenyl or naphthyl which are substituted by lower alkyl, halo-lower alkyl, hydroxy, lower alkoxy, lower alkanoyloxy, halogen, cyano and/or nitro.

Aryl is preferably phenyl which is unsubstituted or substituted as indicated above and, more preferably, phenyl which is substituted by lower alkyl, typically methyl and, most preferably, unsubstituted phenyl.

Lower alkoxy is typically n-propoxy, isopropoxy, n-butoxy or tert-butoxy, preferably ethoxy and methoxy.

Lower alkanoyloxy is typically propionyloxy or pivaloyloxy and, preferably, acetyloxy.

Halogen is typically chloro or fluoro and also bromo and iodo.

Halo-lower alkyl is typically 2- or 3-halo-lower alkyl, such as 2-halo-lower alkyl, e.g. 2-halopropyl, 3-halopropyl or 3-halo-2-methylpropyl and may be, for example, 2-chloropropyl, 3-chloropropyl or 3-chloro-2-methylpropyl.

The organic solvent used in the reaction of this process usefully has a lower boiling point than water. Suitable solvents are typically aromatic hydrocarbons, halogenated hydrocarbons, preferably fluoro- and/or chlorohydrocarbons, cyclic ethers, carboxylic acid esters and ketones. It is possible to use, for example, benzene, methylene chloride, chloroform, trichlorofluoromethane, chloroethane, trifluorotrichloroethane, dichlorotetrafluoroethane, acetone, methyl ethyl ketone, diethyl ketone, cyclohexane, tetrahydrofuran and dioxan, or mixtures of such solvents. Methylene chloride and tetrahydrofuran are particularly preferred.

The process can be carried out by adding the solution of the polysaccharide carbamate, which may be substituted in the aryl moiety, typically polysaccharide-3,5-dimethylphenylcarbamate or polysaccharide phenylcarbamate, dropwise to the aqueous phase, with stirring, and then, with continued stirring, removing the organic solvent, conveniently by distillation and with heating to the boiling point of the solvent and/or under vacuum. The particles are then isolated, typically by filtration or decanting. The particles so obtained are then purified, typically by washing them with a hydrophilic solvent, e.g. a $C_1$–$C_4$alkanol or also with an aqueous mixture thereof.

Washing is preferably carried out with methanol.

The polysaccharide carbamates used in the process of this invention, which may be substituted in the aryl moiety, are obtained by reacting a polysaccharide, typically cellulose or amylose, in a manner known per se with an unsubstituted or substituted aryl isocyanate.

The reaction is preferably carried out with an unsubstituted or substituted phenyl isocyanate.

The carbamate is usually prepared by reaction with a suitable isocyanate in the presence of a suitable catalyst. The catalysts used may be Lewis bases, typically tertiary amines, or also Lewis acids, e.g. a tin compound. The reaction is preferably carried out in the presence of a tertiary base, typically in the presence of pyridine or quinoline serving at the same time as solvents, but it is also preferred to use as tertiary base 4-(N,N-dimethyl-amino)pyridine as a reaction catalyst. The conversion of the OH groups into the corresponding carbamates is preferably carried out with unsubstituted or substituted phenyl isocyanates.

It is preferred to use methyl-substituted, preferably mono- or disubstituted, phenyl isocyanates, or unsubstituted phenyl isocyanates, and the methyl groups can be in meta- or ortho-position to each other.

With the novel process described at the outset, polysaccharide-N-arylcarbamates in rounded or also in irregular shape are surprisingly obtained which have a certain porosity (specific surface area) and a partially crystalline character. This is important with respect to the specific chromatographic separation of enantiomers as a surprisingly high efficiency of separation is achieved in this case.

The invention also relates to the use of the polysaccharide derivatives obtained according to the novel process as stationary phase in chromatographic processes, in particular for separating enantiomers.

The following Examples illustrate the invention in more detail. Temperatures are given in degrees centigrade and pressure, where indicated, is given in bar.

EXAMPLE 1

4 g of cellulose-3,5-dimethylphenylcarbamate are moistened with 15 ml of methanol and then a solution of 12.8 g of N-phenyl-1-heptylcarbamate in 105 ml of methylene chloride is added. This solution is then stirred until the cellulose derivative is completely dissolved. To this solution are then added dropwise 96 ml of a 5% aqueous solution of polyvinyl alcohol (Serva, molecular weight c. 90 000) over 2½ h at room temperature and with vigorous stirring (500 rpm). The emulsion is then slowly heated to 42° C. and the methylene chloride is distilled off (c.2 h). After cooling, the residue is isolated by filtration, washed incrementally with 500 ml of water and then with 200 ml of methanol. The product so obtained is twice in succession suspended in 200 ml of methanol, stirred and isolated by filtration. Subsequently, the product is dried at room temperature.

Yield: 3.7 g.

The material consists of rounded particles having a particle size from 20 to 30 µm. Specific surface area according to BET: 3.7 $M^2$/g.

Column packing:

2.5 g of the material so obtained are suspended in 25 ml of a mixture of hexane/2-propanol (85:15, vol %) and packed by the slurry method into a steel column (25 cm×0.4 cm) at a flow rate of 2 ml/min over 3 h.

EXAMPLE 2

5 g of cellulose phenylcarbamate are moistened with 15 ml of methanol and then a solution of 16 g of N-phenyl-1-heptylcarbamate in 150 ml of methylene chloride is added. This solution is stirred until the cellulose derivative is completely dissolved. To this solution are then added dropwise 120 ml of a 5% aqueous solution of polyvinyl alcohol (Serva, molecular weight c. 90 000) over 2½ h at room temperature and with vigorous stirring (400 rpm). The emulsion is then slowly heated to 42° C. and the methylene chloride is distilled off (c.2 h). After cooling, the residue is isolated by filtration, washed incrementally with 500 ml of water and in conclusion suspended with 200 ml of methanol, stirred and isolated by filtration. Subsequently, the product is dried at room temperature.

Yield: 4.5 g.

The material consists of rounded particles having a particle size from 10 to 30 µM. Specific surface area according to BET: 31.0 $m^2$/g.

Column packing:

2.5 g of the material obtained are suspended in 25 ml of ethanol and stirred for 1 h. The suspension is then subjected to filtration and the filter cake is suspended in 25 ml of a mixture of hexane/2-propanol (90:10, vol %) and packed by the slurry method into a steel column (25 cm×0.4 cm) at a flow rate of 2 ml/min over 3 h.

EXAMPLE 3

5 g of cellulosephenylcarbamate are moistened with 15 ml of methanol and then a solution of 16 g of N-phenyl-1-heptylcarbamate in 300 ml of methylene chloride is added. This solution is stirred until the cellulose derivative is completely dissolved. To this solution are added dropwise 240 ml of a 1% aqueous solution of carboxymethylcellulose (highly viscous) over 2½ h at room temperature and with vigorous stirring (400 rpm). The emulsion is then slowly heated to 42° C. and the methylene chloride is distilled off (c. 2 h). After cooling, the residue is isolated by filtration, washed incrementally with 500 ml of water and in conclusion with 200 ml of methanol. The product so obtained is twice in succession suspended in 200 ml of methanol, stirred and isolated by filtration. Subsequently, the product is dried at room temperature.

Yield: 4.7 g.

The material consists of irregular particles having a particle size of c. 10 μm. Specific surface area according to BET: 5.1 m$^2$/g.

Column packing:

2.5 g of the material so obtained are suspended in 25 ml of ethanol and stirred for 1 h. The suspension is then subjected to filtration and the filter cake is suspended in 25 ml of a mixture of hexane/2-propanol (90:10, vol %) and packed by the slurry method into a steel column (25 cm×0.4 cm ) at a flow rate of 2 ml/min over 3h.

Testing of the chiral stationary phases:

The phases of Examples 1–3 were tested with different racemates (Table 1).

HPL chromatography is in each case carried out with a Shimadzu LC-6A arrangement at a flow rate of 0.7–1 ml/min and at room temperature.

Detection is carried out using UV spectroscopy and polarimetry (Perkin Elmer 241 LC).

The separating factor α was determined as measurement value.

$\alpha = k'_2/k'_1 = (t_2-t_0)/(t_1-t_0)$, where $k'_2$ and $k'_1$ are the capacity factors of the second and first eluted enantiomers, and $t_2$ and $t_1$ are the retention times thereof.

$t_0$ is the elution time of tri-tert-butylbenzene (non-retained compound).

TABLE 1

| | Support | | | | | |
|---|---|---|---|---|---|---|
| | Example 1 | | Example 2 | | Example 3 | |
| Racemate | $k'_1$ | α | $k'_1$ | α | $k'_1$ | α |
| trans-stilbene oxide | 1.32 | 2.19 | 2.78 | 1.34 | 2.1 | 1.55 |
| benzoin | 3.82 | 1.65 | — | — | 19.7 | 1.16 |
| phenylvinyl sulfoxide | — | — | 29.4 | 1.25 | 29.0 | 1.08 |
| flavanone | 2.42 | 1.40 | — | — | 9.23 | 1.09 |
| 2-naphthyl ethanol | 3.28 | 1.80 | — | — | — | — |

What is claimed is:

1. A process for the preparation of a polysaccharide-N-arylcarbamate or a polysaccharide-N-arylcarbamate substituted in the aryl moiety in suitable form as a support for chromatography comprising adding to a polysaccharide N-arylcarbamate or a polysaccharide N-arylcarbamate that is substituted in the aryl moiety, a N-aryl-1-lower-alkyl-carbamate-containing solution of an organic solvent, with vigorous stirring, until the polysaccharide derivative is completely dissolved and then adding thereto an aqueous solution containing a surfactant and, with continued stirring, removing the organic solvent from the emulsion so obtained and isolating the solid particles and washing and drying said particles.

2. A process for the preparation of a polysaccharide-N-phenylcarbamate or a polysaccharide-N-phenylcarbamate substituted in the aryl moiety in suitable form as a support for chromatography comprising adding to a polysaccharide N-phenylcarbamate or a polysaccharide N-phenylcarbamate that is substituted in the aryl moiety, a N-phenyl-heptyl-carbamate-containing solution of an organic solvent, with vigorous stirring, until the polysaccharide derivative is completely dissolved and then adding thereto an aqueous solution containing a surfactant selected from the group consisting of polyvinyl alcohol and carboxymethyl cellulose and, with continued stirring, removing the organic solvent from the emulsion so obtained and isolating the solid particles and washing and drying said particles.

3. The process of claim 1, wherein the organic solvent has a lower boiling point than water.

4. The process of claim 1, wherein the organic solvent is an aromatic hydrocarbon, a halogenated hydrocarbon, a cyclic ether or a ketone.

5. The process of claim 1, wherein the organic solvent is methylene chloride.

6. The process of claim 1, wherein the surfactant is polyvinyl alcohol.

7. The process of claim 1, wherein the high molecular weight surfactant is carboxymethylcellulose.

8. The process of claim 1, wherein the average diameter of the polysaccharide-N-arylcarbamate particles obtained is from 5 to 150 μm.

9. The process of claim 2, wherein the average diameter of the polysaccharide-N-arylcarbamate particles obtained is from 10 to 30 μm.

10. The process of claim 1, wherein the specific surface area of the polysaccharide-N-arylcarbamate particles is from 1 to 100 m$^2$/g.

11. The process of claim 1, wherein the specific surface area of the polysaccharide-N-arylcarbamate particles obtained is from 3 to 35 m$^2$/g.

12. The process of claim 2, wherein the organic solvent has a lower boiling point than water.

13. The process of claim 2, wherein the organic solvent is an aromatic hydrocarbon, a halogenated hydrocarbon, a cyclic ether or a ketone.

14. The process of claim 2, wherein the organic solvent is methylene chloride.

15. The process of claim 2, wherein the surfactant is polyvinyl alcohol.

16. The process of claim 2, wherein the surfactant is carboxymethylcellulose.

17. The process of claim 2, wherein the average diameter of the polysaccharide-N-arylcarbamate particles obtained is from 5 to 150 μm.

18. The process of claim 2, wherein the average diameter of the polysaccharide-N-arylcarbamate particles obtained is from 10 to 30 μm.

19. The process of claim 2, wherein the specific surface area of the polysaccharide-N-arylcarbamate particles is from 1 to 100 m$^2$/g.

20. The process of claim 2, wherein the specific surface area of the polysaccharide-N-arylcarbamate particles obtained is from 3 to 35 m$^2$/g.

21. The process of claim 1 wherein the polysaccharide-N-arylcarbamate is substituted in the aryl moiety with a member selected from the group consisting of lower alkyl, halo-lower alkyl, hydroxy, lower alkoxy, lower alkanoyloxy, halogen, cyano and nitro.

22. The process of claim 2 wherein the polysaccharide-N-phenylcarbamate is substituted in the phenyl moiety with a member selected from the group consisting of lower alkyl, halo-lower alkyl, hydroxy, lower alkoxy, lower alkanoyloxy, halogen, cyano and nitro.

* * * * *